United States Patent [19]

D'Hondt

[11] Patent Number: 4,556,846
[45] Date of Patent: Dec. 3, 1985

[54] EDDY CURRENT TESTING DEVICE WITH A BALANCING DIGITAL MEMORY

[75] Inventor: Jean-Pierre D'Hondt, Tournai, Belgium

[73] Assignee: Intercontrole Societe Anonyme, Rungis, France

[21] Appl. No.: 467,762

[22] Filed: Feb. 18, 1983

[30] Foreign Application Priority Data

Feb. 23, 1982 [BE] Belgium ............................ 892 243

[51] Int. Cl.[4] ...................... G01N 27/82; G01N 27/87
[52] U.S. Cl. .................................. 324/238; 324/202; 324/225
[58] Field of Search ............... 324/225, 227, 232–234, 324/236–240, 202; 340/941

[56] References Cited

U.S. PATENT DOCUMENTS

| | | | |
|---|---|---|---|
| 3,229,198 | 1/1966 | Libby .................................. | 324/233 |
| 3,599,145 | 8/1971 | Ando et al. ......................... | 340/941 |
| 4,207,520 | 6/1980 | Flora et al. ......................... | 324/233 X |
| 4,230,987 | 10/1980 | Mordwinken .................... | 324/233 X |
| 4,326,166 | 4/1982 | Pigeon et al. ..................... | 324/233 X |
| 4,331,920 | 5/1982 | Kalisch et al. ................... | 324/233 X |
| 4,460,869 | 7/1984 | Buser et al. ....................... | 324/227 X |

*Primary Examiner*—Gerard R. Strecker

[57] ABSTRACT

Eddy current non-destructive testing device comprising in per se known manner an exciting generator, a probe connected to the latter, means for sampling in the probe a measuring voltage, means for producing a reference voltage, a differential amplifier having a first and second input and an output, a first input receiving the measuring voltage and the second the reference voltage, digital signal processing means having an input connected to the output of the differential amplifier across an amplifier, said processing means successively comprising an analog—digital converter, a first random access memory and a digital processing circuit, wherein the means for producing a reference voltage comprise a second random access memory having an input and an output, the input being connected to the output of the first random access memory across a switching circuit and a digital—analog converter having an input connected to the output of the memory and an output connected to the second input of the differential amplifier.

2 Claims, 4 Drawing Figures

EDDY CURRENT TESTING DEVICE WITH A BALANCING DIGITAL MEMORY

BACKGROUND OF THE INVENTION

The present invention relates to an eddy current testing device with an electronic balancing loop for use in non-destructive testing.

Non-destructive testing by eddy currents involves producing a variable magnetic field with the aid of a primary winding, subjecting a member to be tested to this magnetic field, sampling a measuring voltage at the terminals of a secondary winding positioned in the vicinity of the tested member and analyzing this voltage. The primary and secondary windings may coincide or may form a bridge. Any defects in the member (change of size, variations in the electrical conductivity, variation in the magnetic permeability, cracks, etc) modifies the phase and intensity of the eddy current circulating in the member and correlatively changes the measuring voltage.

In most cases, the measurement is of a differential nature. For this purpose, a satisfactory standard member is exposed to an identical magnetic field to that to which the member to be tested is exposed and the analyzed voltage is formed by the difference between the voltage corresponding to the tested member and the reference voltage corresponding to the standard. The means making it possible to produce this reference voltage and form the differential voltage constitute the balancing means.

An eddy current non-destructive testing device with balancing means is in the form illustrated in FIG. 1. A sinusoidal signal generator 10 is followed by an amplifier 12, which supplies a probe 14 in the vicinity of which pass the members 16 to be tested. A second probe 14', identical to the first and also excited by amplifier 12, is positioned relative to a standard member 16' in the same way as probe 14 is positioned relative to the members to be tested 16. The voltage sampled at the terminals of probe 14 forms the measuring voltage and that sampled at the terminals of probe 14' the reference voltage.

These voltages are amplified by amplifiers 18, 18', which supply voltages Vm and Vr, which are applied to the two inputs 20/1 and 20/2 of a differential amplifier 20. The latter is followed by a variable gain amplifier 22, connected to signal processing means 24. These means are able to determine the parts of the differential voltage respectively in phase and in phase quadrature with the exciting voltage supplied by the generator 10. However, it can also be a more complex circuit making it possible to determine the Fourier components of the signal. A circuit 26 makes it possible to process the results (storing, recording the results, statistics, etc).

It would appear from FIG. 1 that the probes are constituted by a single winding. However, in practice, they can have several windings (e.g. arranged in bridge-like manner), but the simplification made here has no effect on the understanding of the invention.

With regards to this type of equipment, reference can be made to U.S. Pat. No. 3,229,198 of H. L. LIBBY, granted on Jan. 11th 1966 and entitled "Eddy current nondestructive testing device for measuring multiple parameter variable of a metal sample".

In certain devices of this type, the processing means 24 are of a digital nature. In this case and as illustrated in FIG. 1, they comprise an analog—digital converter 30, followed by a random access memory 32, addressed by a counter 36, connected to a clock 38. The memory is followed by a digital processing circuit 34. If it is a question of calculating the harmonic components of a signal, this circuit performs a discrete Fourier transformation.

The balancing system shown in FIG. 1 has numerous disadvantages:
  it reduces by half the power available for the members to be tested;
  it requires two probes,
  it makes it necessary for the standard to be permanently exposed to the magnetic field, which in the long term leads to a modification of the reference signal (heating of the material, variation of its magnetic properties, etc).

BRIEF SUMMARY OF THE INVENTION

The problem of the present invention is to obviate these disadvantages by proposing electronic balancing means. This object is achieved by forming a reference signal once and for all, by storing this signal and by reproducing it for each measurement so as to compose it with the measuring signal.

The storage of the signal corresponding to the standard member is particularly advantageous in the case of digital equipment, because the latter already has a memory, called the acquisition memory (i.e. memory 32 in FIG. 1) in which are stored samples of the measured signal. It is then merely necessary to store in said memory, the results of the measurements obtained with the standard and then recopy the content of this memory into a second memory to permanently have the reference signal. The first memory is then freed and made available for measurements corresponding to the different samples to be tested. Thus, the standard is only exposed to a single action, the reproduction of the reference signal being obtained electronically. Thus, all the disadvantages referred to hereinbefore are eliminated.

In addition, the invention has the following advantage. In the prior art, there are two measuring channels (probe 14—amplifier 18 on the one hand and probe 14'—amplifier 18' on the other). However, such channels cannot be strictly identical. Thus, the differential signal supplied by amplifier 20 contains a part which is due to the unbalance between the two channels. According to the invention, the circuit only comprises a single measuring channel, which is used twice, firstly with the standard member and then with the various members to be tested. Therefore, possible defects of the analysis channel will be perfectly compensated, because they will have the same effects on the measuring and reference signals.

The present invention more specifically relates to an eddy current non-destructive testing device comprising in per se known manner an exciting generator, a probe connected to the latter, means for sampling in the probe a measuring voltage, means for producing a reference voltage, a differential amplifier having a first and a second input and an output, the first input receiving the measuring voltage and the second the reference voltage, digital signal processing means having an input connected to the output of the differential amplifier across an amplifier, said processing means successively comprising an analog—digital converter, a first random access memory and a digital processing circuit, wherein the means for producing a reference voltage comprise a second random access memory having an input and an output, the input being connected to the output of the first random access memory across a switching circuit and a digital—analog converter having an input connected to the output of the memory and an output connected to the second input of the differential amplifier.

BRIEF DESCRIPTION OF THE DRAWINGS

The features and advantages of the present invention will become more apparent from the following description of non-limitative embodiments and with reference to the attached drawings, following the already described FIG. 1, and wherein show.

DETAILED DESCRIPTION OF THE PREFERRED EMBODIMENTS

Figure 1:
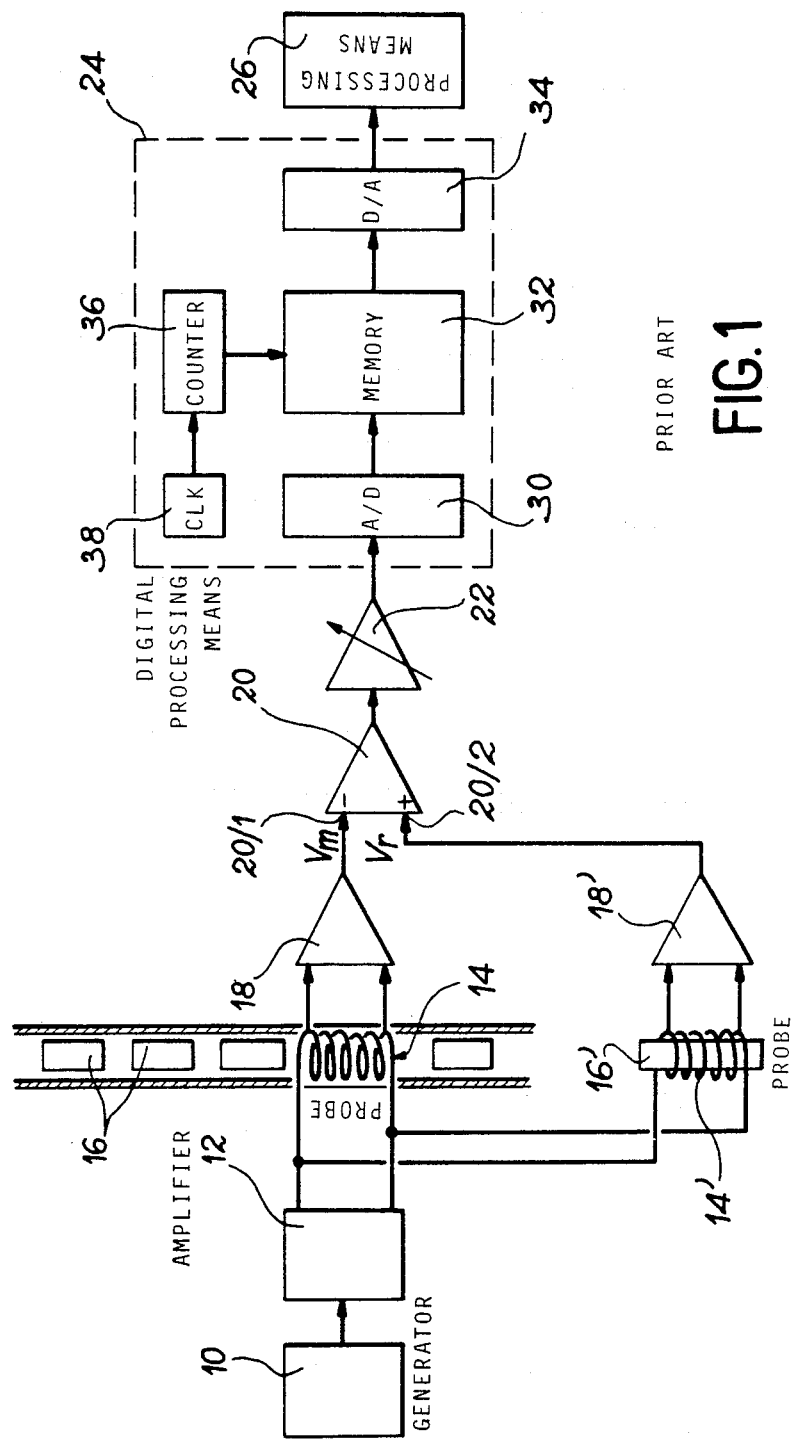
Figure 2:
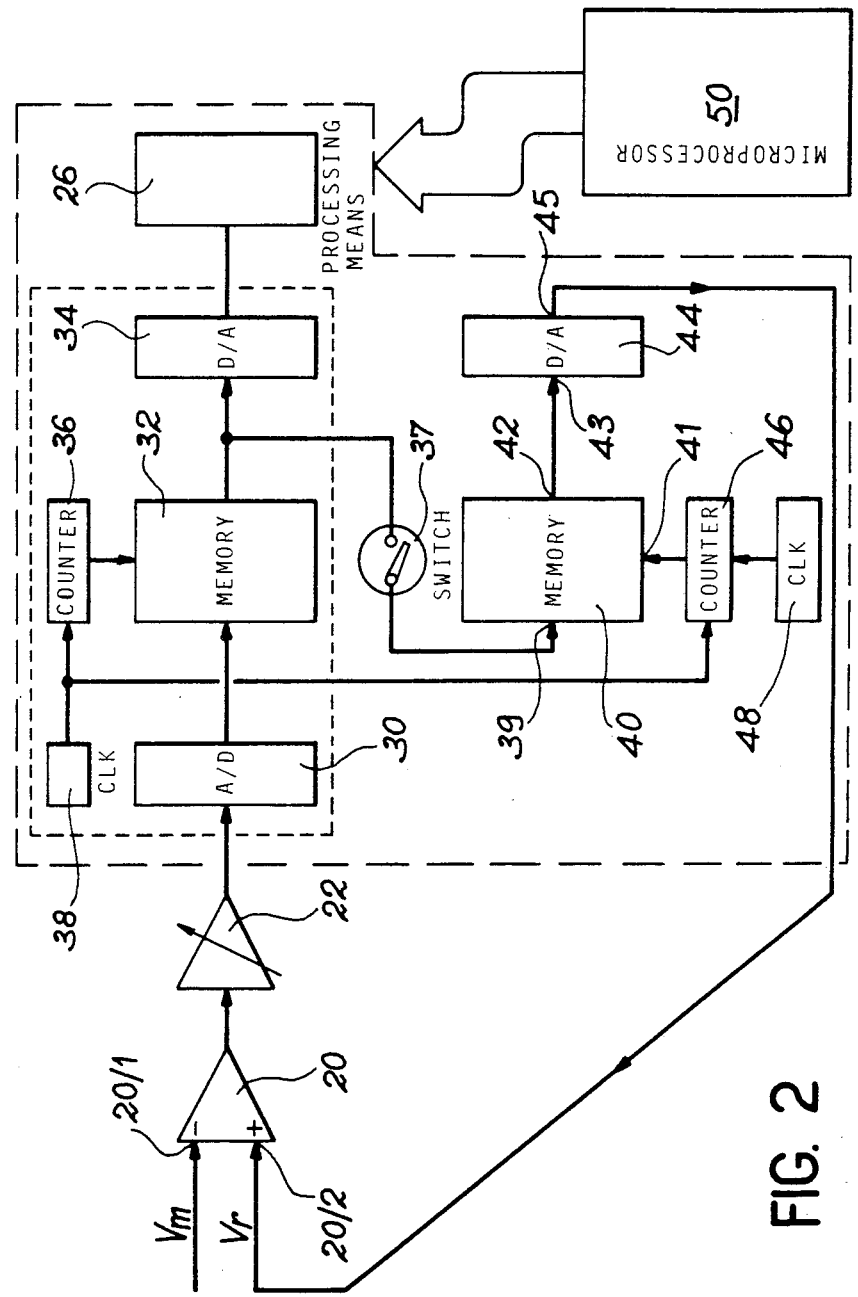
FIG. 2 a block diagram of the balancing means used in the invention.

In the diagram of FIG. 2, it is possible to see the elements already represented in FIG. 1 and which for this reason carry the same references, mainly the analog—digital converter 30, the acquisition memory 32 addressed by a counter 36, which is itself controlled by a clock 38 and the computing circuit 34. FIG. 2 also shows balancing means constituted by a second memory 40, identical to the acquisition memory 32. The second memory has a data input 39 connected to the output of acquisition memory 32 by a switching circuit 37, an addressing input 41 and an output 42. There is a digital—analog converter 44 having an input 43 connected to the output 42 of the memory and an output 45 connected to the second input 20/2 of the differential amplifier 20. The means shown also comprise a counter 46 connected to the addressing input 41, and which receives pulses from clock 38. A circuit 48 permits the preloading of the counter to an initial content.

The circuits shown may also incorporate a microprocessor 50, which controls all or part of the aforementioned components, in accordance with informatics processes which are well known in the art and which do not form part of the invention. Furthermore, said microprocessor is only useful in the case of very high performance equipment.

The operation of this circuit is readily apparent from what has been stated hereinbefore. When the standard member is disposed in the measuring probe, the digital signal recorded in memory 32 is in fact the reference signal. This signal is formed by N digital samples, which requires N memory locations. Each location is defined by an address and each address corresponds to a particular content of counter 36. In the writing phase, the content of this counter passes progressively from 0 to N-1 under the control of clock 38 and the N samples are sequentially written at the N corresponding addresses.

The content of the acquisition memory 32 is then recopied into the balancing memory 40. This operation is very simple as a result of the duplication of the counting and storage elements. Thus, counter 46, like counter 36, is controlled by clock 48, so that the addressing of a sample to be read in the acquisition memory is simultaneously accompanied by the addressing of the sample to be written into the balancing memory 40.

Naturally, the reading and writing addresses can be staggered, if circuit 48 imposes an initial content differing from zero on counter 46.

Throughout the recopying operation, switching circuit 37 is closed. Then, when the reference signal is written into memory 40, switch 37 is open and memory 32 becomes available for the writing and reading of the data corresponding to the members to be tested.

Figure 3:
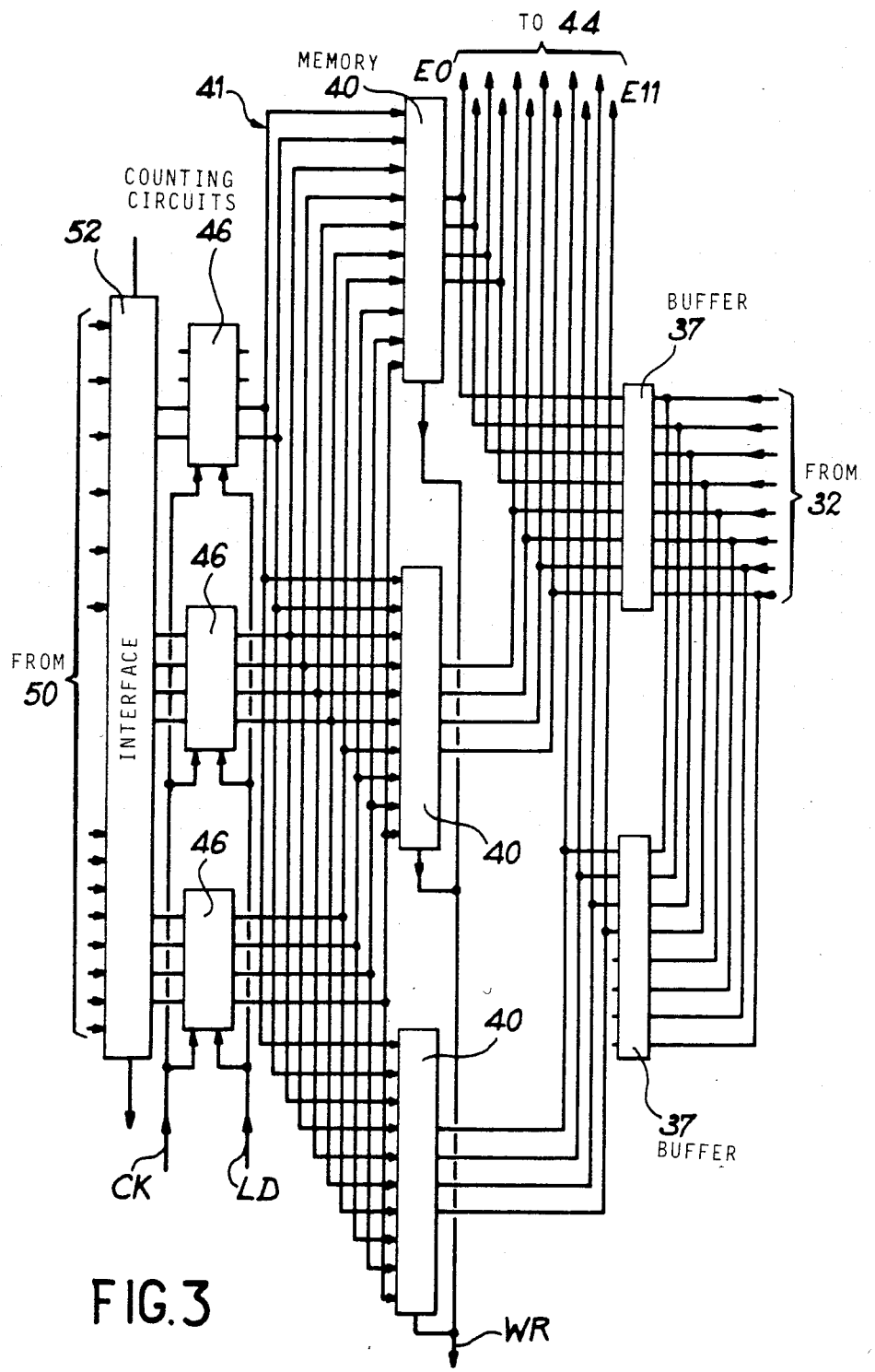
FIG. 3 an embodiment of a balancing memory.
Figure 4:
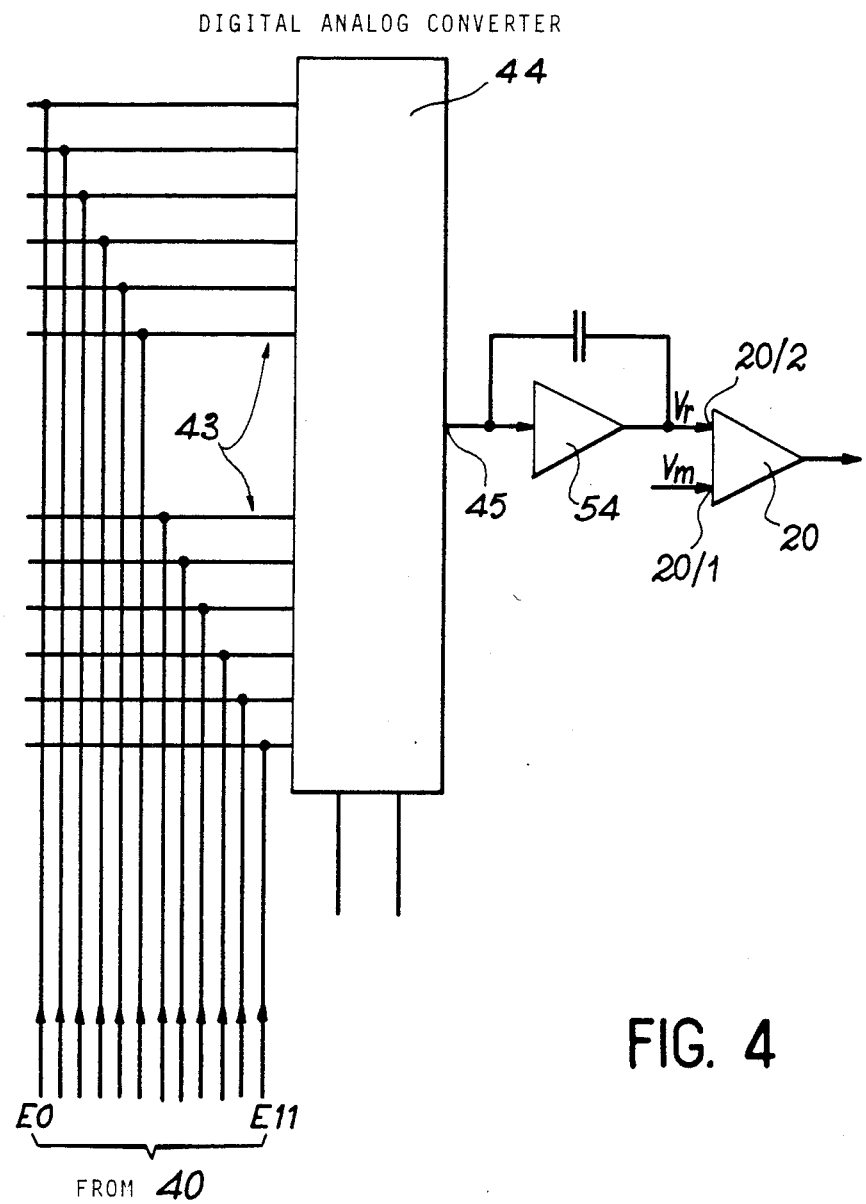
FIG. 4 an embodiment of the digital—analog converter.

It is readily apparent that the connections indicated in FIG. 2 are diagrammatic and that in reality it involves a bus with several connections. In the same way, switch 37 which is shown in highly diagrammatic form is in fact an electronic circuit able to carry several bits. The aim of FIGS. 3 and 4 is to give a more realistic idea of these means. These drawings correspond to a special embodiment corresponding to a device operating in the range 3 to 3000 Hz with 512 samples, each sample being coded on 12 bits.

FIG. 3 shows the balancing memory 40 formed by three memory circuits, e.g. of type 2148 H, each of these circuits operating on 4 bits. The data output and input take place from the right. Reading and writing are controlled by a connection WR. In the case of writing, the data pass through circuit 37 formed by two bidirectional buffer circuits, e.g. of type 8304, said circuits having 8 inputs connected to the acquisition memory 32 and 8 outputs, whereof only 4 are used for one of them. The addressing of the memory takes place from the left as a result of counter 46, which is formed by three counting circuits, e.g. of type 74LS191. These counters operate in each case on 4 bits, which makes it possible, by only using 2 bits for one of the counters, to form 10 bit addresses. 9 bit addresses are used for addressing one of the 512 samples ($2^9=512$) and the 10th is used for the resetting of the counter. The counters have a clock connection CK and a loading control connection LD. The 12 data bits read in memory 40 are carried by 12 connections E0 to E11 directed towards the digital—analog converter 44.

The counter is preceded by an interface circuit 52, e.g. of type 8255, which makes it possible for the microprocessor to reload the counter to the initial content.

FIG. 4 shows the digital—analog converter 44 receiving the 12 bits from balancing memory 40. This converter can be of type AD 565. At output 45, it supplies a current, which is converted into a voltage by a current-voltage converter 54. It is the voltage supplied by the latter circuit which forms the reference voltage Vr applied to the input 20/2 of the differential amplifier 20.

What is claimed is:

1. An eddy current non-destructive testing device comprising an exciting generator, a probe connected to the latter, an amplifier having two inputs connected to the probe and an output supplying a measuring voltage, a differential amplifier having a first and a second input and an output, the first input receiving the measuring voltage, a variable gain amplifier having an input connected to the output of the differential amplifier, said amplifier having an output, an analog—digital converter having an input connected to said output of said amplifier and having an output, a first random access memory having an input connected to the output of said analog—digital converter, and an output, a second random access memory having an input and an output, a switching circuit being connected between the output of the first random access memory and the input of said second random access memory and a digital analog converter having an input connected to the output of the second random access memory and an output connected to the second input of said differential amplifier.

2. A device according to claim 1, wherein each memory is addressed by a counter and a clock.

* * * * *